(12) United States Patent
Brangwynne et al.

(10) Patent No.: US 12,195,768 B2
(45) Date of Patent: Jan. 14, 2025

(54) SYSTEM AND METHOD FOR MODULATING STRESS GRANULE ASSEMBLY

(71) Applicant: The Trustees of Princeton University, Princeton, NJ (US)

(72) Inventors: Cliff Brangwynne, Hopewell, NJ (US); Victoria Drake, Quaker Hill, CT (US); David Sanders, Princeton, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 936 days.

(21) Appl. No.: 17/258,783

(22) PCT Filed: Jul. 12, 2019

(86) PCT No.: PCT/US2019/041564
§ 371 (c)(1),
(2) Date: Jan. 8, 2021

(87) PCT Pub. No.: WO2020/014588
PCT Pub. Date: Jan. 16, 2020

(65) Prior Publication Data
US 2021/0269780 A1    Sep. 2, 2021

Related U.S. Application Data

(60) Provisional application No. 62/719,751, filed on Aug. 20, 2018, provisional application No. 62/697,691, filed on Jul. 13, 2018.

(51) Int. Cl.
| | | |
|---|---|---|
| *C12N 9/14* | (2006.01) | |
| *A61K 9/00* | (2006.01) | |
| *A61K 38/00* | (2006.01) | |

(52) U.S. Cl.
CPC .............. *C12N 9/14* (2013.01); *A61K 9/0019* (2013.01); *A61K 9/0085* (2013.01);
(Continued)

(58) Field of Classification Search
CPC ................ A61K 38/00; C07K 2319/00; C07K 2319/60; C12N 9/14; C12Y 306/04012
See application file for complete search history.

(56) References Cited

U.S. PATENT DOCUMENTS

2006/0058505 A1* 3/2006 Kennedy ................ C07K 14/47
435/325
2015/0164891 A1* 6/2015 Hornstein ............ A61K 31/496
514/253.04
(Continued)

FOREIGN PATENT DOCUMENTS

| JP | 2005514912 A | 5/2005 |
|---|---|---|
| JP | 2016535600 A | 11/2016 |

(Continued)

OTHER PUBLICATIONS

Office Action for corresponding Japanese Application No. 2021-523576, dated Jan. 5, 2023.
(Continued)

*Primary Examiner* — David W Berke-Schlessel
*Assistant Examiner* — Trent R Clarke
(74) *Attorney, Agent, or Firm* — MEAGHER EMANUEL LAKS GOLDBERG & LIAO, LLP

(57) ABSTRACT

A system and method for modulating stress granule assembly, utilizing a protein construct that has a cell penetrating protein fused to one or more proteins that can bind with an NTF2-like domain of a G3BP protein. By configuring the protein construct with an appropriate number of proteins that being with NTF2-like domains, stress granule assembly can be upregulated or downregulated as needed to treat patients.

13 Claims, 7 Drawing Sheets
Specification includes a Sequence Listing.

(52) U.S. Cl.
CPC ...... *C12Y 306/04012* (2013.01); *A61K 38/00* (2013.01); *C07K 2319/00* (2013.01); *C07K 2319/60* (2013.01)

(56) References Cited

U.S. PATENT DOCUMENTS

| 2017/0145394 | A1 | 5/2017 | Yeo et al. |
| 2019/0127428 | A1* | 5/2019 | Taylor ............ C12Y 306/04012 |
| 2020/0360467 | A1* | 11/2020 | Twiss ..................... A61K 38/10 |

FOREIGN PATENT DOCUMENTS

| JP | 2020520947 | A | 7/2020 |
| WO | 2003018630 | A1 | 3/2003 |
| WO | 2007132555 | A1 | 9/2009 |
| WO | 2013108926 | A1 | 7/2013 |
| WO | 2015063452 | A2 | 5/2015 |
| WO | 2017161096 | A1 | 9/2017 |
| WO | 2018215597 | A1 | 11/2018 |
| WO | 2020014588 | A1 | 1/2020 |

OTHER PUBLICATIONS

Panas, Marc D. et al., "Viral and Cellular Proteins Containing FGDF Motifs Bind G3BP to Block Stress Granule Formation," PLOS Pathogens, vol. 11, No. 2, e1004659, Feb. 6, 2015.

International Search Report and Written Opinion for PCT/US2019/041115, dated Sep. 13, 2019.

Zhang et al., "GAP161 Targets and Downregulates G3BP to Suppress Cell Growth and Potentiate Cisplaitin-Mediated Cytotoxicity to Colon Carcinoma HCT116 Cells", Cancer Sci, Oct. 2012, vol. 103, No. 10, pp. 1848-1856.

Vognsen et al., "Crystal Structures of the Human G3BP1 NTF2-Like Domain Visualize FxFG Nup Repeat Specificity", PLoS One, Dec. 4, 2013, vol. 8, No. 12:e80947, pp. 1-9.

Solomon et al., "Distinct Structural Features of Caprin-1 Mediate Its Interaction with G3BP-1 and Its Induction of Phosphorylation of Eukaryotic Translation Initiation Factor 2a, Entry to Cytoplasmic Stress Granules, and Selective Interaction with a Subset of mRNAs", Molecular and Cellular Biology, 2007, vol. 27, No. 6, pp. 2324-2342.

English translation of Chinese second office action for corresponding CN Application No. 201980046655.3, dated Feb. 7, 2024.

* cited by examiner

SEQUENCE LISTING

<160> NUMBER OF SEQ ID NOS: 9

<210> SEQ ID NO 1
<211> LENGTH: 15
<212> TYPE: PRT
<213> ORGANISM: Artificial Sequence
<220> FEATURE:
<223> OTHER INFORMATION: TAT

<400> SEQUENCE: 1

Cys Gly Arg Lys Lys Arg Arg Gln Arg Arg Pro Pro Gln Cys
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Penetratin

<400> SEQUENCE: 2

Arg Gln Ile Lys Ile Trp Phe Gln Asn Arg Arg Met Lys Trp Lys Lys
1               5                   10                  15

<210> SEQ ID NO 3
<211> LENGTH: 466
<212> TYPE: PRT
<213> ORGANISM: Homo sapiens

<400> SEQUENCE: 3

Met Val Met Glu Lys Pro Ser Pro Leu Leu Val Gly Arg Glu Phe Val
1               5                   10                  15

Arg Gln Tyr Tyr Thr Leu Leu Asn Gln Ala Pro Asp Met Leu His Arg
                20                  25                  30

Phe Tyr Gly Lys Asn Ser Ser Tyr Val His Gly Gly Leu Asp Ser Asn
            35                  40                  45

Gly Lys Pro Ala Asp Ala Val Tyr Gly Gln Lys Glu Ile His Arg Lys
        50                  55                  60

Val Met Ser Gln Asn Phe Thr Asn Cys His Thr Lys Ile Arg His Val
65                  70                  75                  80

Asp Ala His Ala Thr Leu Asn Asp Gly Val Val Val Gln Val Met Gly
                85                  90                  95

Leu Leu Ser Asn Asn Asn Gln Ala Leu Arg Arg Phe Met Gln Thr Phe
            100                 105                 110

Val Leu Ala Pro Glu Gly Ser Val Ala Asn Lys Phe Tyr Val His Asn
        115                 120                 125

Asp Ile Phe Arg Tyr Gln Asp Glu Val Phe Gly Gly Phe Val Thr Glu
    130                 135                 140

Pro Gln Glu Glu Ser Glu Glu Val Glu Glu Pro Glu Glu Arg Gln
145                 150                 155                 160

Gln Thr Pro Glu Val Val Pro Asp Asp Ser Gly Thr Phe Tyr Asp Gln
                165                 170                 175

Ala Val Val Ser Asn Asp Met Glu Glu His Leu Glu Glu Pro Val Ala
            180                 185                 190

Glu Pro Glu Pro Asp Pro Glu Pro Gln Glu Pro Val Ser
        195                 200                 205

Glu Ile Gln Glu Glu Lys Pro Glu Pro Val Leu Glu Glu Thr Ala Pro
    210                 215                 220

Glu Asp Ala Gln Lys Ser Ser Ser Pro Ala Pro Ala Asp Ile Ala Gln

```
                225                 230                 235                 240
        Thr Val Gln Glu Asp Leu Arg Thr Phe Ser Trp Ala Ser Val Thr Ser
                        245                 250                 255
        Lys Asn Leu Pro Pro Ser Gly Ala Val Pro Val Thr Gly Ile Pro Pro
                        260                 265                 270
        His Val Lys Val Pro Ala Ser Gln Pro Arg Pro Glu Ser Lys Pro
                        275                 280                 285
        Glu Ser Gln Ile Pro Pro Gln Arg Pro Gln Arg Asp Gln Arg Val Arg
                290                 295                 300
        Glu Gln Arg Ile Asn Ile Pro Pro Gln Arg Gly Pro Arg Pro Ile Arg
        305                 310                 315                 320
        Glu Ala Gly Glu Gln Gly Asp Ile Glu Pro Arg Arg Met Val Arg His
                                325                 330                 335
        Pro Asp Ser His Gln Leu Phe Ile Gly Asn Leu Pro His Glu Val Asp
                        340                 345                 350
        Lys Ser Glu Leu Lys Asp Phe Phe Gln Ser Tyr Gly Asn Val Val Glu
                        355                 360                 365
        Leu Arg Ile Asn Ser Gly Gly Lys Leu Pro Asn Phe Gly Phe Val Val
                370                 375                 380
        Phe Asp Asp Ser Glu Pro Val Gln Lys Val Leu Ser Asn Arg Pro Ile
        385                 390                 395                 400
        Met Phe Arg Gly Glu Val Arg Leu Asn Val Glu Glu Lys Lys Thr Arg
                                405                 410                 415
        Ala Ala Arg Glu Gly Asp Arg Arg Asp Asn Arg Leu Arg Gly Pro Gly
                        420                 425                 430
        Gly Pro Arg Gly Gly Leu Gly Gly Met Arg Gly Pro Pro Arg Gly
                        435                 440                 445
        Gly Met Val Gln Lys Pro Gly Phe Gly Val Gly Arg Gly Leu Ala Pro
                        450                 455                 460
        Arg Gln
        465

<210> SEQ ID NO 4
<211> LENGTH: 482
<212> TYPE: PRT
<213> ORGANISM: Homo sapiens

<400> SEQUENCE: 4

Met Val Met Glu Lys Pro Ser Pro Leu Leu Val Gly Arg Glu Phe Val
        1               5                   10                  15
        Arg Gln Tyr Tyr Thr Leu Leu Asn Lys Ala Pro Glu Tyr Leu His Arg
                        20                  25                  30
        Phe Tyr Gly Arg Asn Ser Ser Tyr Val His Gly Gly Val Asp Ala Ser
                        35                  40                  45
        Gly Lys Pro Gln Glu Ala Val Tyr Gly Gln Asn Asp Ile His His Lys
                50                  55                  60
        Val Leu Ser Leu Asn Phe Ser Glu Cys His Thr Lys Ile Arg His Val
        65                  70                  75                  80
        Asp Ala His Ala Thr Leu Ser Asp Gly Val Val Gln Val Met Gly
                        85                  90                  95
        Leu Leu Ser Asn Ser Gly Gln Pro Glu Arg Lys Phe Met Gln Thr Phe
                        100                 105                 110
        Val Leu Ala Pro Glu Gly Ser Val Pro Asn Lys Phe Tyr Val His Asn
                        115                 120                 125
```

Asp Met Phe Arg Tyr Glu Asp Glu Val Phe Gly Asp Ser Glu Pro Glu
130             135                 140

Leu Asp Glu Glu Ser Glu Asp Glu Val Glu Glu Gln Glu Glu Arg
145                 150                 155                 160

Gln Pro Ser Pro Glu Pro Val Gln Glu Asn Ala Asn Ser Gly Tyr Tyr
                165                 170                 175

Glu Ala His Pro Val Thr Asn Gly Ile Glu Glu Pro Leu Glu Glu Ser
            180                 185                 190

Ser His Glu Pro Glu Pro Glu Pro Glu Ser Glu Thr Lys Thr Glu Glu
                195                 200                 205

Leu Lys Pro Gln Val Glu Glu Lys Asn Leu Glu Leu Glu Glu Lys
210                 215                 220

Ser Thr Thr Pro Pro Pro Ala Glu Pro Val Ser Leu Pro Gln Glu Pro
225                 230                 235                 240

Pro Lys Ala Phe Ser Trp Ala Ser Val Thr Ser Lys Asn Leu Pro Pro
                245                 250                 255

Ser Gly Thr Val Ser Ser Ser Gly Ile Pro Pro His Val Lys Ala Pro
                260                 265                 270

Val Ser Gln Pro Arg Val Glu Ala Lys Pro Glu Val Gln Ser Gln Pro
                275                 280                 285

Pro Arg Val Arg Glu Gln Arg Pro Arg Glu Arg Pro Gly Phe Pro Pro
290                 295                 300

Arg Gly Pro Arg Pro Gly Arg Gly Asp Met Glu Gln Asn Asp Ser Asp
305                 310                 315                 320

Asn Arg Arg Ile Ile Arg Tyr Pro Asp Ser His Gln Leu Phe Val Gly
                325                 330                 335

Asn Leu Pro His Asp Ile Asp Glu Asn Glu Leu Lys Glu Phe Phe Met
                340                 345                 350

Ser Phe Gly Asn Val Val Glu Leu Arg Ile Asn Thr Lys Gly Val Gly
                355                 360                 365

Gly Lys Leu Pro Asn Phe Gly Phe Val Val Phe Asp Asp Ser Glu Pro
370                 375                 380

Val Gln Arg Ile Leu Ile Ala Lys Pro Ile Met Phe Arg Gly Glu Val
385                 390                 395                 400

Arg Leu Asn Val Glu Glu Lys Lys Thr Arg Ala Ala Arg Glu Arg Glu
                405                 410                 415

Thr Arg Gly Gly Gly Asp Asp Arg Arg Asp Ile Arg Arg Asn Asp Arg
                420                 425                 430

Gly Pro Gly Gly Pro Arg Gly Ile Val Gly Gly Met Met Arg Asp
                435                 440                 445

Arg Asp Gly Arg Gly Pro Pro Pro Arg Gly Met Ala Gln Lys Leu
450                 455                 460

Gly Ser Gly Arg Gly Thr Gly Gln Met Glu Gly Arg Phe Thr Gly Gln
465                 470                 475                 480

Arg Arg

<210> SEQ ID NO 5
<211> LENGTH: 27
<212> TYPE: PRT
<213> ORGANISM: Artificial Sequence
<220> FEATURE:
<223> OTHER INFORMATION: USP10 FGDF Motif x1

<400> SEQUENCE: 5

Pro Gln Tyr Ile Phe Gly Asp Phe Ser Pro Asp Glu Phe Asn Gln Phe

```
                1               5                   10                  15
Phe Val Thr Pro Arg Ser Ser Val Glu Leu Pro
                20                  25

<210> SEQ ID NO 6
<211> LENGTH: 62
<212> TYPE: PRT
<213> ORGANISM: Artificial Sequence
<220> FEATURE:
<223> OTHER INFORMATION: USP10 FGDF Motif x2

<400> SEQUENCE: 6

Pro Gln Tyr Ile Phe Gly Asp Phe Ser Pro Asp Glu Phe Asn Gln Phe
1               5                   10                  15

Phe Val Thr Pro Arg Ser Ser Val Glu Leu Pro Ser Ser Gly Ser Gly
                20                  25                  30

Ser Gly Ser Pro Gln Tyr Ile Phe Gly Asp Phe Ser Pro Asp Glu Phe
            35                  40                  45

Asn Gln Phe Phe Val Thr Pro Arg Ser Ser Val Glu Leu Pro
        50                  55                  60

<210> SEQ ID NO 7
<211> LENGTH: 1087
<212> TYPE: PRT
<213> ORGANISM: Homo sapiens

<400> SEQUENCE: 7

Met Met Thr Ser Val Gly Thr Asn Arg Ala Arg Gly Asn Trp Glu Gln
1               5                   10                  15

Pro Gln Asn Gln Asn Gln Thr Gln His Lys Gln Arg Pro Gln Ala Thr
                20                  25                  30

Ala Glu Gln Ile Arg Leu Ala Gln Met Ile Ser Asp His Asn Asp Ala
            35                  40                  45

Asp Phe Glu Glu Lys Val Lys Gln Leu Ile Asp Ile Thr Gly Lys Asn
        50                  55                  60

Gln Asp Glu Cys Val Ile Ala Leu His Asp Cys Asn Gly Asp Val Asn
65                  70                  75                  80

Arg Ala Ile Asn Val Leu Leu Glu Gly Asn Pro Asp Thr His Ser Trp
                85                  90                  95

Glu Met Val Gly Lys Lys Lys Gly Val Ser Gly Gln Lys Asp Gly Gly
                100                 105                 110

Gln Thr Glu Ser Asn Glu Glu Gly Lys Glu Asn Arg Asp Arg Asp Arg
            115                 120                 125

Asp Tyr Ser Arg Arg Gly Gly Pro Pro Arg Arg Gly Arg Gly Ala
        130                 135                 140

Ser Arg Gly Arg Glu Phe Arg Gly Gln Glu Asn Gly Leu Asp Gly Thr
145                 150                 155                 160

Lys Ser Gly Gly Pro Ser Gly Arg Gly Thr Glu Arg Gly Arg Arg Gly
                165                 170                 175

Arg Gly Arg Gly Arg Gly Ser Gly Arg Arg Gly Gly Arg Phe Ser
                180                 185                 190

Ala Gln Gly Met Gly Thr Phe Asn Pro Ala Asp Tyr Ala Glu Pro Ala
            195                 200                 205

Asn Thr Asp Asp Asn Tyr Gly Asn Ser Ser Gly Asn Thr Trp Asn Asn
        210                 215                 220

Thr Gly His Phe Glu Pro Asp Asp Gly Thr Ser Ala Trp Arg Thr Ala
225                 230                 235                 240
```

```
Thr Glu Glu Trp Gly Thr Glu Asp Trp Asn Glu Asp Leu Ser Glu Thr
              245                 250                 255

Lys Ile Phe Thr Ala Ser Asn Val Ser Val Pro Leu Pro Ala Glu
          260                 265                 270

Asn Val Thr Ile Thr Ala Gly Gln Arg Ile Asp Leu Ala Val Leu Leu
              275                 280                 285

Gly Lys Thr Pro Ser Thr Met Glu Asn Asp Ser Ser Asn Leu Asp Pro
              290                 295                 300

Ser Gln Ala Pro Ser Leu Ala Gln Pro Leu Val Phe Ser Asn Ser Lys
305                 310                 315                 320

Gln Thr Ala Ile Ser Gln Pro Ala Ser Gly Asn Thr Phe Ser His His
              325                 330                 335

Ser Met Val Ser Met Leu Gly Lys Gly Phe Gly Asp Val Gly Glu Ala
              340                 345                 350

Lys Gly Gly Ser Thr Thr Gly Ser Gln Phe Leu Glu Gln Phe Lys Thr
              355                 360                 365

Ala Gln Ala Leu Ala Gln Leu Ala Ala Gln His Ser Gln Ser Gly Ser
              370                 375                 380

Thr Thr Thr Ser Ser Trp Asp Met Gly Ser Thr Thr Gln Ser Pro Ser
385                 390                 395                 400

Leu Val Gln Tyr Asp Leu Lys Asn Pro Ser Asp Ser Ala Val His Ser
              405                 410                 415

Pro Phe Thr Lys Arg Gln Ala Phe Thr Pro Ser Ser Thr Met Met Glu
              420                 425                 430

Val Phe Leu Gln Glu Lys Ser Pro Ala Val Ala Thr Ser Thr Ala Ala
              435                 440                 445

Pro Pro Pro Pro Ser Ser Pro Leu Pro Ser Lys Ser Thr Ser Ala Pro
              450                 455                 460

Gln Met Ser Pro Gly Ser Ser Asp Asn Gln Ser Ser Pro Gln Pro
465                 470                 475                 480

Ala Gln Gln Lys Leu Lys Gln Lys Lys Ala Ser Leu Thr Ser
              485                 490                 495

Lys Ile Pro Ala Leu Ala Val Glu Met Pro Gly Ser Ala Asp Ile Ser
              500                 505                 510

Gly Leu Asn Leu Gln Phe Gly Ala Leu Gln Phe Gly Ser Glu Pro Val
              515                 520                 525

Leu Ser Asp Tyr Glu Ser Thr Pro Thr Thr Ser Ala Ser Ser Ser Gln
              530                 535                 540

Ala Pro Ser Ser Leu Tyr Thr Ser Thr Ala Ser Glu Ser Ser Ser Thr
545                 550                 555                 560

Ile Ser Ser Asn Gln Ser Gln Glu Ser Gly Tyr Gln Ser Gly Pro Ile
              565                 570                 575

Gln Ser Thr Thr Tyr Thr Ser Gln Asn Asn Ala Gln Gly Pro Leu Tyr
              580                 585                 590

Glu Gln Arg Ser Thr Gln Thr Arg Arg Tyr Pro Ser Ser Ile Ser Ser
              595                 600                 605

Ser Pro Gln Lys Asp Leu Thr Gln Ala Lys Asn Gly Phe Ser Ser Val
              610                 615                 620

Gln Ala Thr Gln Leu Gln Thr Gln Ser Val Glu Gly Ala Thr Gly
625                 630                 635                 640

Ser Ala Val Lys Ser Asp Ser Pro Ser Thr Ser Ser Ile Pro Pro Leu
              645                 650                 655
```

```
Asn Glu Thr Val Ser Ala Ala Ser Leu Leu Thr Thr Asn Gln His
            660                 665                 670

Ser Ser Ser Leu Gly Gly Leu Ser His Ser Glu Glu Ile Pro Asn Thr
    675                 680                 685

Thr Thr Thr Gln His Ser Ser Thr Leu Ser Thr Gln Gln Asn Thr Leu
690                 695                 700

Ser Ser Ser Thr Ser Ser Gly Arg Thr Ser Thr Ser Thr Leu Leu His
705                 710                 715                 720

Thr Ser Val Glu Ser Glu Ala Asn Leu His Ser Ser Ser Ser Thr Phe
                725                 730                 735

Ser Thr Thr Ser Ser Thr Val Ser Ala Pro Pro Val Val Ser Val
            740                 745                 750

Ser Ser Ser Leu Asn Ser Gly Ser Ser Leu Gly Leu Ser Leu Gly Ser
            755                 760                 765

Asn Ser Thr Val Thr Ala Ser Thr Arg Ser Ser Val Ala Thr Thr Ser
770                 775                 780

Gly Lys Ala Pro Pro Asn Leu Pro Pro Gly Val Pro Pro Leu Leu Pro
785                 790                 795                 800

Asn Pro Tyr Ile Met Ala Pro Gly Leu Leu His Ala Tyr Pro Pro Gln
                805                 810                 815

Val Tyr Gly Tyr Asp Asp Leu Gln Met Leu Gln Thr Arg Phe Pro Leu
                820                 825                 830

Asp Tyr Tyr Ser Ile Pro Phe Pro Thr Pro Thr Pro Leu Thr Gly
            835                 840                 845

Arg Asp Gly Ser Leu Ala Ser Asn Pro Tyr Ser Gly Asp Leu Thr Lys
    850                 855                 860

Phe Gly Arg Gly Asp Ala Ser Ser Pro Ala Pro Ala Thr Thr Leu Ala
865                 870                 875                 880

Gln Pro Gln Gln Asn Gln Thr Gln Thr His His Thr Thr Gln Gln Thr
                885                 890                 895

Phe Leu Asn Pro Ala Leu Pro Pro Gly Tyr Ser Tyr Thr Ser Leu Pro
            900                 905                 910

Tyr Tyr Thr Gly Val Pro Gly Leu Pro Ser Thr Phe Gln Tyr Gly Pro
    915                 920                 925

Ala Val Phe Pro Val Ala Pro Thr Ser Ser Lys Gln His Gly Val Asn
    930                 935                 940

Val Ser Val Asn Ala Ser Ala Thr Pro Phe Gln Gln Pro Ser Gly Tyr
945                 950                 955                 960

Gly Ser His Gly Tyr Asn Thr Gly Val Ser Val Thr Ser Ser Asn Thr
                965                 970                 975

Gly Val Pro Asp Ile Ser Gly Ser Val Tyr Ser Lys Thr Gln Gln Ser
            980                 985                 990

Phe Glu Lys Gln Gly Phe His Ser Gly Thr Pro Ala Ala Ser Phe Asn
    995                 1000                1005

Leu Pro Ser Ala Leu Gly Ser Gly Gly Pro Ile Asn Pro Ala Thr
            1010                1015                1020

Ala Ala Ala Tyr Pro Pro Ala Pro Phe Met His Ile Leu Thr Pro
            1025                1030                1035

His Gln Gln Pro His Ser Gln Ile Leu His His His Leu Gln Gln
            1040                1045                1050

Asp Gly Gln Thr Gly Ser Gly Gln Arg Ser Gln Thr Ser Ser Ile
            1055                1060                1065

Pro Gln Lys Pro Gln Thr Asn Lys Ser Ala Tyr Asn Ser Tyr Ser
```

Trp Gly Ala Asn
    1085

<210> SEQ ID NO 8
<211> LENGTH: 709
<212> TYPE: PRT
<213> ORGANISM: Homo sapiens

<400> SEQUENCE: 8

Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Gly Ala
            20                  25                  30

Gly Ala Ala Ala Pro Ala Ser Gln His Pro Ala Thr Gly Thr Gly Ala
                35                  40                  45

Val Gln Thr Glu Ala Met Lys Gln Ile Leu Gly Val Ile Asp Lys Lys
    50                  55                  60

Leu Arg Asn Leu Glu Lys Lys Gly Lys Leu Asp Asp Tyr Gln Glu
65                  70                  75                  80

Arg Met Asn Lys Gly Glu Arg Leu Asn Gln Asp Gln Leu Asp Ala Val
                85                  90                  95

Ser Lys Tyr Gln Glu Val Thr Asn Asn Leu Glu Phe Ala Lys Glu Leu
            100                 105                 110

Gln Arg Ser Phe Met Ala Leu Ser Gln Asp Ile Gln Lys Thr Ile Lys
        115                 120                 125

Lys Thr Ala Arg Arg Glu Gln Leu Met Arg Glu Ala Glu Gln Lys
    130                 135                 140

Arg Leu Lys Thr Val Leu Glu Leu Gln Tyr Val Leu Asp Lys Leu Gly
145                 150                 155                 160

Asp Asp Glu Val Arg Thr Asp Leu Lys Gln Gly Leu Asn Gly Val Pro
                165                 170                 175

Ile Leu Ser Glu Glu Leu Ser Leu Leu Asp Glu Phe Tyr Lys Leu
            180                 185                 190

Val Asp Pro Glu Arg Asp Met Ser Leu Arg Leu Asn Glu Gln Tyr Glu
        195                 200                 205

His Ala Ser Ile His Leu Trp Asp Leu Leu Glu Gly Lys Glu Lys Pro
    210                 215                 220

Val Cys Gly Thr Thr Tyr Lys Val Leu Lys Glu Ile Val Glu Arg Val
225                 230                 235                 240

Phe Gln Ser Asn Tyr Phe Asp Ser Thr His Asn His Gln Asn Gly Leu
                245                 250                 255

Cys Glu Glu Glu Ala Ala Ser Ala Pro Ala Val Gly Asp Gln Val
            260                 265                 270

Pro Glu Ala Glu Pro Glu Pro Ala Glu Glu Tyr Thr Glu Gln Ser Glu
        275                 280                 285

Val Glu Ser Thr Glu Tyr Val Asn Arg Gln Phe Met Ala Glu Thr Gln
    290                 295                 300

Phe Thr Ser Gly Glu Lys Glu Gln Val Asp Glu Trp Thr Val Glu Thr
305                 310                 315                 320

Val Glu Val Val Asn Ser Leu Gln Gln Gln Pro Gln Ala Ala Ser Pro
                325                 330                 335

Ser Val Pro Glu Pro His Ser Leu Thr Pro Val Ala Gln Ala Asp Pro
            340                 345                 350

-continued

Leu Val Arg Arg Gln Arg Val Gln Asp Leu Met Ala Gln Met Gln Gly
        355                 360                 365

Pro Tyr Asn Phe Ile Gln Asp Ser Met Leu Asp Phe Glu Asn Gln Thr
    370                 375                 380

Leu Asp Pro Ala Ile Val Ser Ala Gln Pro Met Asn Pro Thr Gln Asn
385                 390                 395                 400

Met Asp Met Pro Gln Leu Val Cys Pro Pro Val His Ser Glu Ser Arg
            405                 410                 415

Leu Ala Gln Pro Asn Gln Val Pro Val Gln Pro Glu Ala Thr Gln Val
                420                 425                 430

Pro Leu Val Ser Ser Thr Ser Glu Gly Tyr Thr Ala Ser Gln Pro Leu
        435                 440                 445

Tyr Gln Pro Ser His Ala Thr Glu Gln Arg Pro Gln Lys Glu Pro Ile
    450                 455                 460

Asp Gln Ile Gln Ala Thr Ile Ser Leu Asn Thr Asp Gln Thr Thr Ala
465                 470                 475                 480

Ser Ser Ser Leu Pro Ala Ala Ser Gln Pro Gln Val Phe Gln Ala Gly
            485                 490                 495

Thr Ser Lys Pro Leu His Ser Ser Gly Ile Asn Val Asn Ala Ala Pro
                500                 505                 510

Phe Gln Ser Met Gln Thr Val Phe Asn Met Asn Ala Pro Val Pro Pro
        515                 520                 525

Val Asn Glu Pro Glu Thr Leu Lys Gln Gln Asn Gln Tyr Gln Ala Ser
    530                 535                 540

Tyr Asn Gln Ser Phe Ser Ser Gln Pro His Gln Val Glu Gln Thr Glu
545                 550                 555                 560

Leu Gln Gln Glu Gln Leu Gln Thr Val Val Gly Thr Tyr His Gly Ser
            565                 570                 575

Pro Asp Gln Ser His Gln Val Thr Gly Asn His Gln Gln Pro Pro Gln
                580                 585                 590

Gln Asn Thr Gly Phe Pro Arg Ser Asn Gln Pro Tyr Tyr Asn Ser Arg
        595                 600                 605

Gly Val Ser Arg Gly Gly Ser Arg Gly Ala Arg Gly Leu Met Asn Gly
    610                 615                 620

Tyr Arg Gly Pro Ala Asn Gly Phe Arg Gly Gly Tyr Asp Gly Tyr Arg
625                 630                 635                 640

Pro Ser Phe Ser Asn Thr Pro Asn Ser Gly Tyr Thr Gln Ser Gln Phe
            645                 650                 655

Ser Ala Pro Arg Asp Tyr Ser Gly Tyr Gln Arg Asp Gly Tyr Gln Gln
                660                 665                 670

Asn Phe Lys Arg Gly Ser Gly Gln Ser Gly Pro Arg Gly Ala Pro Arg
        675                 680                 685

Gly Arg Gly Gly Pro Pro Arg Pro Asn Arg Gly Met Pro Gln Met Asn
    690                 695                 700

Thr Gln Gln Val Asn
705

<210> SEQ ID NO 9
<211> LENGTH: 324
<212> TYPE: PRT
<213> ORGANISM: Homo sapiens

<400> SEQUENCE: 9

Met Ser Ser Glu Ala Glu Thr Gln Gln Pro Pro Ala Ala Pro Pro Ala
1               5                   10                  15

```
Ala Pro Ala Leu Ser Ala Ala Asp Thr Lys Pro Gly Thr Thr Gly Ser
            20                  25                  30
Gly Ala Gly Ser Gly Gly Pro Gly Gly Leu Thr Ser Ala Ala Pro Ala
        35                  40                  45
Gly Gly Asp Lys Lys Val Ile Ala Thr Lys Val Leu Gly Thr Val Lys
    50                  55                  60
Trp Phe Asn Val Arg Asn Gly Tyr Gly Phe Ile Asn Arg Asn Asp Thr
65                      70                  75                  80
Lys Glu Asp Val Phe Val His Gln Thr Ala Ile Lys Lys Asn Asn Pro
                85                  90                  95
Arg Lys Tyr Leu Arg Ser Val Gly Asp Gly Glu Thr Val Glu Phe Asp
            100                 105                 110
Val Val Glu Gly Glu Lys Gly Ala Glu Ala Ala Asn Val Thr Gly Pro
            115                 120                 125
Gly Gly Val Pro Val Gln Gly Ser Lys Tyr Ala Ala Asp Arg Asn His
    130                 135                 140
Tyr Arg Arg Tyr Pro Arg Arg Gly Pro Pro Arg Asn Tyr Gln Gln
145                 150                 155                 160
Asn Tyr Gln Asn Ser Glu Ser Gly Glu Lys Asn Glu Gly Ser Glu Ser
                165                 170                 175
Ala Pro Glu Gly Gln Ala Gln Gln Arg Arg Pro Tyr Arg Arg Arg Arg
            180                 185                 190
Phe Pro Pro Tyr Tyr Met Arg Arg Pro Tyr Gly Arg Arg Pro Gln Tyr
            195                 200                 205
Ser Asn Pro Pro Val Gln Gly Glu Val Met Glu Gly Ala Asp Asn Gln
    210                 215                 220
Gly Ala Gly Glu Gln Gly Arg Pro Val Arg Gln Asn Met Tyr Arg Gly
225                 230                 235                 240
Tyr Arg Pro Arg Phe Arg Arg Gly Pro Pro Arg Gln Arg Gln Pro Arg
            245                 250                 255
Glu Asp Gly Asn Glu Glu Asp Lys Glu Asn Gln Gly Asp Glu Thr Gln
            260                 265                 270
Gly Gln Gln Pro Pro Gln Arg Arg Tyr Arg Arg Asn Phe Asn Tyr Arg
            275                 280                 285
Arg Arg Arg Pro Glu Asn Pro Lys Pro Gln Asp Gly Lys Glu Thr Lys
            290                 295                 300
Ala Ala Asp Pro Pro Ala Glu Asn Ser Ser Ala Pro Glu Ala Glu Gln
305                 310                 315                 320
Gly Gly Ala Glu
```

SYSTEM AND METHOD FOR MODULATING STRESS GRANULE ASSEMBLY

CROSS-REFERENCE TO RELATED APPLICATIONS

This application claims priority to U.S. Provisional Application No. 62/697,691, filed Jul. 13, 2018, and U.S. Provisional Application No. 62/719,751, filed Aug. 20, 2018, both of which are herein incorporated by reference in their entirety.

REFERENCE TO SEQUENCE LISTING

The present application is being filed along with a Sequence Listing in electronic format. The Sequence Listing is provided as a file entitled PRIN-63876 ST25.TXT, created Jul. 11, 2019, which is approximately 28,287 bytes in size. The information in the electronic format of the Sequence Listing is incorporated herein by reference in its entirety.

FIELD OF THE INVENTION

The present invention relates to a system and method for treating individuals to modulate the assembly of stress granules in the individual, and specifically for providing particular proteins that modulate dimerization and other interactions associated with G3BP1/2 and other key stress granule proteins in a way that allows for the up- and down-regulation of stress granule assembly.

BACKGROUND

G3BP refers to two homologous human proteins termed G3BP1 and G3BP2. G3BP includes an RNA-binding domain (RBD), an internal disordered region, and a dimerization/oligomerization domain. In G3BP, the dimerization/oligomerization domain consists of amino acids 1-142 of G3BP1 or amino acids 1-133 of G3BP2 (hereinafter referred to as "NTF2-like" domains). Data suggests that viruses interfere with oligomerization of G3BP1/2 to prevent the formation of stress granules, which typically act as platforms to relay protective cell death-initiating signals to prevent continued viral replication.

Stress granules are micron-sized membrane-less condensates composed of RNA and protein that form, e.g., upon stressful environmental perturbations. Persistent stress granule assembly or perturbed dynamics likely plays a critical role in initiating the characteristic protein pathology observed in neurodegenerative diseases such as amyotrophic lateral sclerosis (ALS), frontotemporal degeneration (FTD), inclusion body myopathies (IBM), and potentially Alzheimer's disease (AD). Not surprisingly, various cancers have evolved related strategies to promote tumor viability, counter-intuitively by stabilizing critical RNAs via G3BP upregulation. Thus, there is an urgent public health need to develop rationally designed therapeutic approaches that interfere with the assembly or dynamics of stress granules.

Currently, treatments that prevent, cure, or prolong lifespan are non-existent in the context of human neurodegenerative diseases. Brain diseases associated with perturbed RNA homeostasis represent a particularly formidable challenge, since most are caused by conversion of an essential physiological protein (e.g., TDP43) to a self-replicating form that ultimately kills the brain cell (i.e., neuron) via protein loss-of-function or poorly understood gain-of-function. A simple strategy proposed for many neurodegenerative diseases associated with such "protein misfolding" is to get rid of the toxic protein using genetic strategies. This is a viable approach for diseases caused by proteins that feature redundancy with respect to their function or are not important for the adult nervous system. Unfortunately, however, most proteins that accumulate in diseases of RNA homeostasis (e.g., ALS, FTD, IBM) are essential RNA-binding molecules with diverse cellular functions. Proximal proteins (e.g., G3BP) in the formation of stress granules are similarly problematic targets. Thus, therapeutics aimed at reducing their levels (e.g., siRNA, shRNA, antisense oligonucleotides) are likely to cause significant unwanted consequences if used in patients.

Thus, a system and method for modulating stress granule assembly is desirable.

BRIEF SUMMARY

A first aspect of the present disclosure is a protein construct that can be used to modulate stress granule assembly. The protein construct is configured to penetrate a cell and bind with the G3BP1 (or G3BP2) NTF2-like domain. To do so, the protein construct includes a cell penetrating protein fused to between 1 and 10 additional proteins that dimerize with a NTF2 domain or interact with dimerized NTF2-like domains, where the additional proteins could be one or more of: the first m amino acids of G3BP1 where m is between 8 and 334, and preferably between 8 and 142, the first n amino acids of G3BP2 where n is between 8 and 330, and preferably between 8 and 133, or a peptide variant having any of the forms: (1) $X_y$-FGDF-$X_y$; (2) $X_y$-FGEF-$X_y$; or (3) $X_y$-FGSF-$X_y$, where $X_y$ is 1 to y additional amino acids. In some embodiments, y≤1500, y≤1000, y≤500, y≤100, y≤50. In preferred embodiments, y≤25. In more preferred embodiments, y≤10. Optionally, the cell penetrating protein may also be fused to a protein tag, such as a fluorescent protein. A plasmid may be constructed that expresses the protein construct.

A second aspect of the present disclosure is a method for treating patients with a disease or infection. The method involves providing a protein construct configured to penetrate a cell and bind with an NTF2-like domain or NTF2-like dimer, such as the protein construct described previously. The protein construct is then appropriately introduced to the patient, such as by injecting a solution or other fluid containing the protein construct at a location that allows the protein fragment to modulate pathological stress granule assembly, where the protein construct may be in a solution or other fluid. The protein construct is then allowed to penetrate a cell and interact with at least one NTF2-like monomer or dimer within the cell. Where the protein construct is configured to only bind with a single NTF2-like domain, such dimerization will diminish the formation of stress granules. Where the protein construct is configured to simultaneously interact with two or more NTF2-like domains, such interactions will upregulate the formation of stress granules, by facilitating the formation of a connected network of interactions required for phase separation and stress granule condensation. Optionally, the patient will have a neurodegenerative disease or disorder of cell proliferation (e.g., various cancers). Optionally, the protein construct may be injected into cerebrospinal fluid. Optionally, the protein construct may hinder at least one homotypic or heterotypic interaction in the organism between an essential stress granule nucleator and the protein construct or associating binding partners without causing immediate cell toxicity. Optionally, the protein construct may be introduced as a prophylactic treatment. Optionally, the protein construct may be introduced as an active treatment of a viral infection.

DETAILED DESCRIPTION

As used herein, articles such as "a" and "an" when used in a claim, are understood to mean one or more of what is claimed or described.

As used herein, the term "about [a number]" is intended to include values rounded to the appropriate significant digit. Thus, "about 1" would be intended to include values between 0.5 and 1.5, whereas "about 1.0" would be intended to include values between 0.95 and 1.05.

As used herein, the term "at least one" means one or more and thus includes individual components as well as mixtures/combinations.

As used herein, the terms "include", "includes" and "including" are meant to be non-limiting.

As used herein, the term "cell penetrating protein" is meant to include both cell penetrating proteins and cell penetrating peptides.

G3BP can exist as dimers that interact with a number of additional RNA-binding proteins via its NTF2-like dimerization domain to form large-scale phase-separated or aggregated biomolecular condensates/assemblies. In stressed cells, such assemblies, organized around G3BP dimers via interactions with the NTF2-like domain, recruit other components such as ribosomal subunits and RNA, which enter the system following stress-dependent ribosome disassembly. The end result of this process is the formation of micron-sized RNA-protein assemblies ("stress granules") that can be observed by microscopy. The continued presence of stress granules can impair physiology and cause the characteristic protein pathologies observed in neurodegenerative diseases such as ALS. Alternatively, they may promote cell viability in rapidly proliferating cells associated with cancer. Stress granules are primarily composed of RNA but also contain characteristic RNA-binding proteins and oligomerized G3BP.

The disclosed system and method seek to treat diverse human diseases by preventing the first step in stress granule assembly (G3BP dimerization or complex formation with other RNA-binding proteins via NTF2-like domain binding interface) while minimizing unwanted side effects or toxicity associated with genetic ablation of the protein culprits driving disease pathogenesis.

G3BP is an essential nucleator of stress granule assembly. The RBD and NTF2-like domain are both critical to its function in the assembly of stress granules. The present disclosure takes advantage of the discovery that the assembly of stress granules can be modulated by introducing specifically configured protein constructs that are used to bind with the NTF2-like domains.

Figure 1:
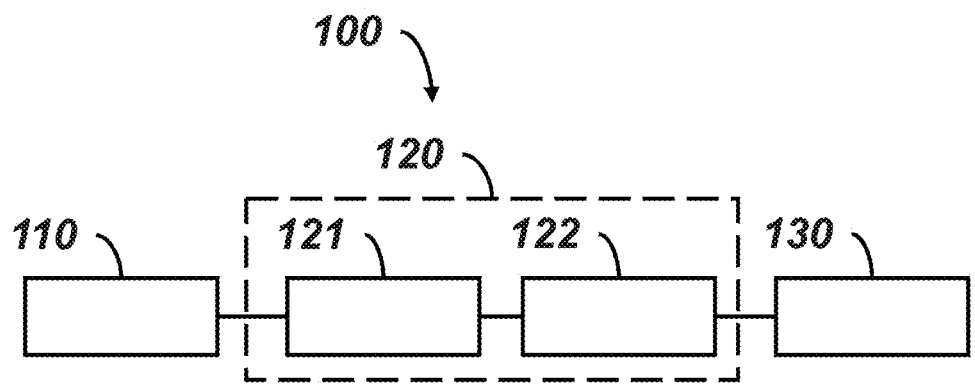
FIG. 1 is a schematic of an embodiment of a protein construct, where a cell penetrating protein is fused to two binding proteins and an optional tagging protein.

A first aspect of the present disclosure is a protein construct that can be used to modulate stress granule assembly. Referring to FIG. 1, the protein construct (100) is generally configured to have at least two segments, where the first segment (110) is fused to the second segment (120). The first segment (110) comprises a sequence that allows the construct to penetrate a cell. The second segment (120) comprises one or more sequences or fragments (121, 122) that can bind with an NTF2-like domain in a G3BP1 or G3BP2 protein. A third, optional segment (130) that comprises a protein tag, may also be fused to the first group (110).

The first segment (110) should comprise a cell penetrating protein (CPP). Any appropriate CPP known to those of skill in the art are envisioned. As an example, the CPP may be a positively charged peptide and may be selected from the group consisting of (1) trans-activator of transcription (TAT) (SEQ ID NO: 1), (b) penetratin (SEQ ID NO: 2), (c) polyarginine, (d) polylysine, or (e) an oligopeptide comprising at least about 70% of histidine, lysine, and/or arginine. In addition, the CPP may comprise a protein transduction domain (PTD) and may also be a cell permeable protein.

The second segment (120) should comprise between 1 and 10 additional proteins ("binding proteins") (121, 122) (as used herein, "proteins" includes both full-length proteins and protein fragments) that can bind with the NTF2-like domain in a G3BP1 or G3BP2 protein. In some preferred embodiments, the number of additional binding proteins is 1 or 2. While the additional binding proteins may be identical, they may also each be a different full-length protein or protein fragment.

The second segment (120) specifically modulate the formation of stress granules (i.e. G3BP dimerization or oligomerization of it and associated proteins), preferably without disrupting RNA-binding protein abundance.

Figure 2:
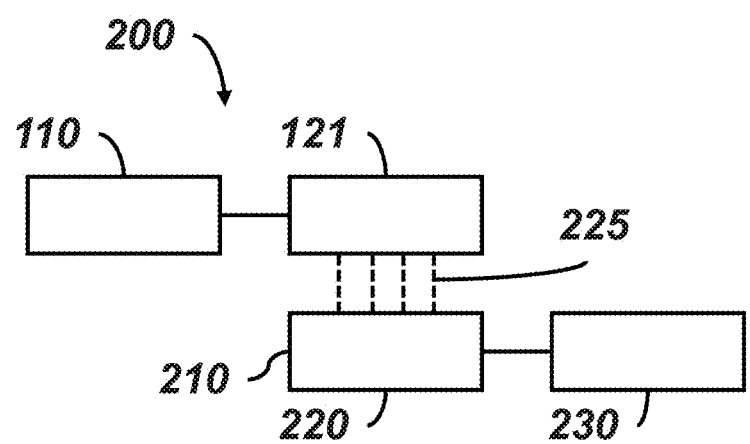
FIG. 2 is a schematic of a protein construct with a single binding protein interacting with a G3BP1 protein.
Figure 3:
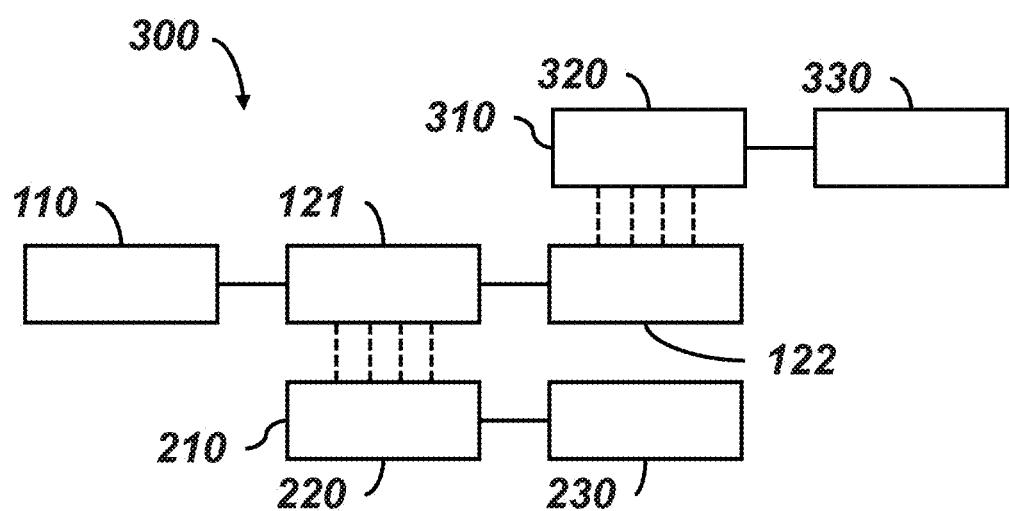
FIG. 3 is a schematic of a protein construct with two binding proteins interacting with two G3BP1 proteins.
Figure 4:
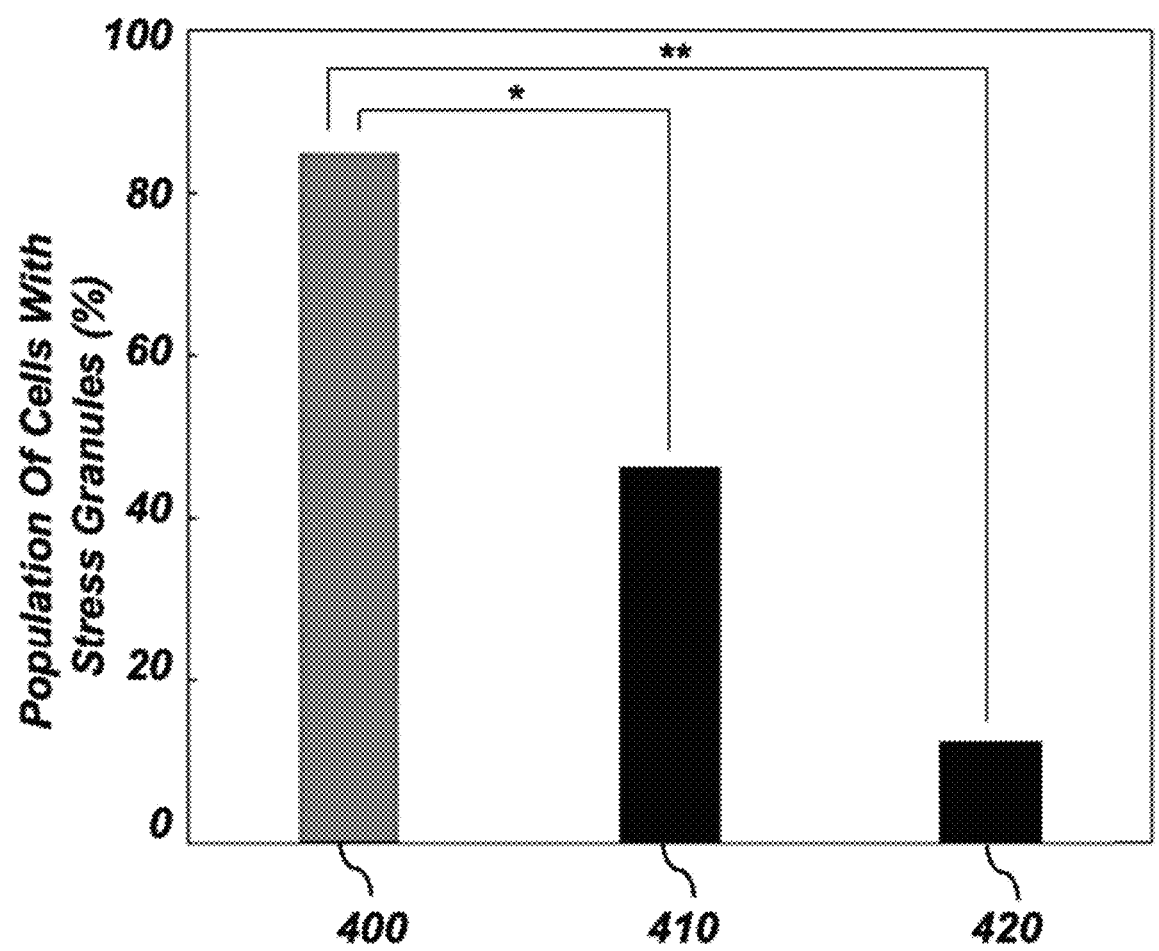
FIG. 4 is a graph indicating the impact of binding proteins on the formation of stress granules, comparing the percentage of cells with stress granules for (i) cells that do not express G3BPdi (400), (ii) all cells expressing G3BPdi (410), and (iii) only cells expressing relatively high concentrations of G3BPdi (420).

Referring to FIG. 2, a system (200) is shown that includes a construct comprising a first segment having a cell penetrating protein (110) fused to a single binding protein in a second segment (121). The single binding protein in the second segment (121) binds (225) to the NTF2-like domain (220) of a G3BP1 protein (210). As can be seen, the protein construct does not interfere with the RNA-binding domain (230) of the G3BP1 protein. In this configuration, where the second segment consists of a single binding protein that can bind with the NTF2-like domain, stress granule assembly is down-regulated. Said differently, protein constructs in this configuration allow the single binding protein to act as a "cap" to prevent a G3BP protein from binding to a second G3BP protein, thus preventing the formation of a core around which a stress granule could nucleate.

Referring to FIG. 3, a system (300) is shown that includes a construct comprising a first segment (110) fused to a second segment, where the second segment contains a first binding protein (121) and a second binding protein (122) for binding to NTF2-like domains. The first binding protein (121) binds to the NTF2-like domain (220) of one G3BP1 protein (210), while the second binding protein (122) binds to the NTF2-like domain (320) of another G3BP1 protein (310). As can be seen, the protein construct does not interfere with either RNA-binding domain (230, 330) of the G3BP1 proteins. In this configuration, where the second group consists of multiple binding proteins that can bind with NTF2-like domains, stress granule assembly is upregulated. Said differently, constructs in this configuration target the most proximal step of stress granule biogenesis and mimic a similar self-protective or self-replicative approach used by viral proteins to evade the immune system and replicate.

The additional binding proteins may include, but are not limited to, (i) the first m amino acids of G3BP1 (SEQ ID NO: 3) where m is between 8 and 334 (a sequence consisting of the first 334 amino acids can be referred to as G3BP1 ΔRBD), and preferably between 8 and 142; or (ii) the first n amino acids of G3BP2 (SEQ ID NO: 4) where m is between 8 and 330 (a sequence consisting of the first 330 amino acids can be referred to as G3BP2 ΔRBD), and preferably between 8 and 133. A sequence consisting of the first 142 amino acids of G3BP1 is hereinafter referred to as "G3BPdi" (G3BP dimer inhibitor).

In action, these binding proteins can be used to modulate the formation of stress granules. In one example, human HEK293 cells expressing a fluorescent marker of stress granules (PABPC1-EYFP) were treated with 1 mM sodium arsenite for 2 hours. Cells expressing a negative control (mCherry-sspB, a fluorescent fusion protein) were used and compared to cells expressing the negative control placed on the end of G3BPdi (G3BPdi-mCherry-sspB). After the sodium arsenite treatment, the percentage of cells with stress granules was quantified.

Referring to FIG. 4, the percentage of cells featuring PABPC1-positive stress granules were manually counted based on confocal microscopy images taken after sodium arsenite treatment (SA). In the absence of SA, no cells featured stress granules (data not shown). In control cells (mCh-SSPB) (400), stress granules were observed in 85% of cells (N=40). Cells expressing the experimental 142-amino acid peptide (G3BPdi-mCh-SSPB) (410) were significantly less likely to feature such granules (46% of cells, N=39). If only cells expressing relatively high concentrations of G3BPdi are considered (420), even fewer cells feature stress granules (~13% of cells, N=8). This data suggests a dose-dependent effect of the fragment under investigation. The asterisks indicate statistical significance (*=p-value of 0.0003, **=p-value of <0.0001). These results prove that G3BPdi significantly inhibits stress granule formation.

However, since at high expression levels, cell growth defects and occasional cell death was observed, preferred G3BP fragments have less than 142 amino acids. Based on structural knowledge of G3BP-substrate binding, other appropriate proteins can be identified. For example, two factors (USP10 and CAPRIN1) that tune stress granule dynamics, compete for binding at specific interfaces in the first 124 amino acids of G3BP. Further, viral proteins featuring FGDF peptides, and possibly also related FGEF and FGSF are thought to perturb G3BP oligomerization at similar locations.

With this understanding, the additional binding proteins may alternatively utilize specific amino acid residues from G3BP1, G3BP2, USP10 and/or viral proteins with FGDF-motifs, where those specific amino acid residues may be important for oligomerization and/or interaction with other proteins that mediate higher-order complex assembly.

It is believed that these specific amino acid residues from G3BP1/2 may include K5, L10, V11, F15, R32, F33, K123, and F124. As such, peptide variants that specifically target these residues may also be utilized. In some embodiments, all eight residues are preferentially bound. In some embodiments, seven of the eight residues are bound. In some embodiments, six of the eight residues are bound. In some embodiments, five of the eight residues are bound. In some embodiments, four of the eight residues are bound.

The additional binding proteins from USP10 and/or viral proteins with FGDF-motifs may include, but are not limited to, a peptide variant having any of the forms: (1) $X_y$-FGDF-$X_y$; (2) $X_y$-FGEF-$X_y$; or (3) $X_y$-FGSF-$X_y$, where $X_y$ is 1 to y additional amino acids. In some embodiments, y≤1500, y≤1000, y≤500, y≤100, y≤50. In preferred embodiments, y≤20. In more preferred embodiments, y≤10.

Referring back to FIG. 1, the optional third segment (130) comprises a protein tag. Any appropriate protein tag may be utilized, including affinity tags, chromatography tags, fluorescence tags, etc., depending on the needs of a given application. Often, a fluorescence tag is utilized, such as mCherry, GFP, or EYFP, is used. In FIG. 1, the third group is shown at the far right of the protein construct, but if a protein tag is used, it may appear anywhere in the construct, the tags do not have to be the same, and they may be positioned throughout the construct. For example, a construct could have a structure that follows the general form of: CPP-GFP-Binding Protein-EYFP-Binding Protein-mCherry.

DNA fragments encoding sequences of interest, without the cell penetrating proteins, were amplified by PCR with Phusion® High-Fidelity DNA Polymerase (NEB). Oligonucleotides used for PCR were synthesized by IDT. In-Fusion HD cloning kit (Clonetech) was used to insert the PCR amplified fragments into (A) AscI (NEB restriction enzyme)-linearized FM5-mGFP-AscI site vector; (B) AscI (NEB restriction enzyme)-linearized FM5-mCherry-AscI site vector; and (C) AscI (NEB restriction enzyme)-linearized FM5-miRFP670-AscI site vector. Cloning products were confirmed by GENEWIZ sequencing, sequencing from both ends of the insert. In addition to a stop sequence after each insert, inserts included: (A) G3BP1 NTF2-like domain (the first 142 amino acids in G3BP1); (B) G3BP1 ΔRBD (the first 334 amino acids in G3BP1); (C) USP10 FGDF motif ×1 [PQYIFGDFSP DEFNQFFVTPRSSVELP] (SEQ ID NO: 5); and (D) USP10 FGDF motif ×2 [PQYIFGDFSP DEFNQFFVTPRSSVELPSSGSGSGS PQYIFGDFSP DEFNQFFVTP RSSVELP] (SEQ ID NO: 6). A cell penetrating protein can be incorporated into the inserts above, using standard, known techniques.

Figure 7A:
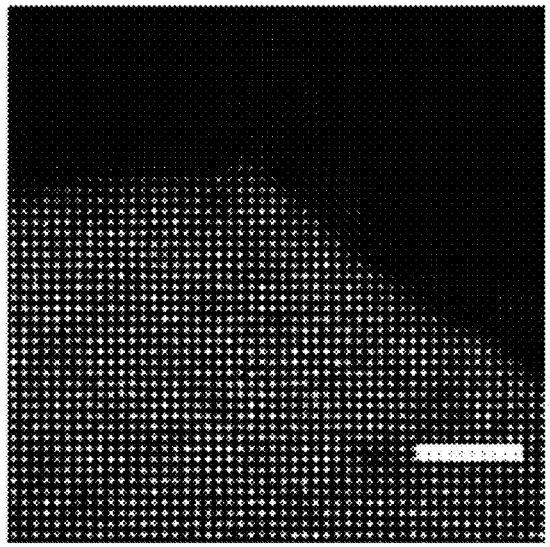
FIG. 7A is an image of G3BP1/2 double-knockout U2OS cells expressing high mGFP-UBAP2L 467-540 after arsenite treatment, illustrating the lack of stress granules.
Figure 7B:
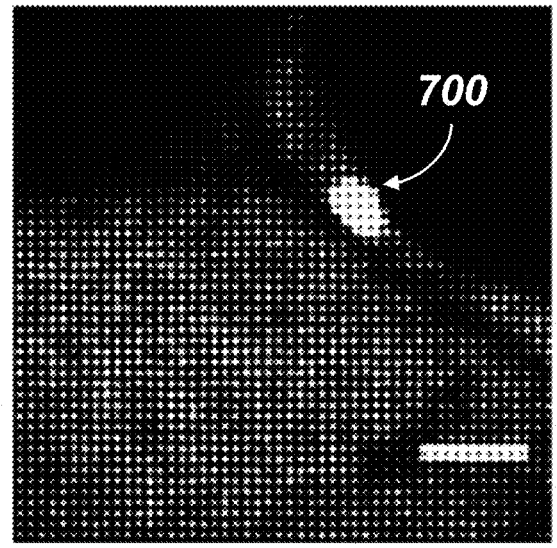
FIG. 7B is an image of G3BP1/2 double-knockout U2OS cells expressing low mGFP-UBAP2L 467-540 after arsenite treatment, illustrating the formation of stress granules (700).

In an example illustrating the ability to reduce stress granule assembly, G3BP1 and UBAP2L (SEQ ID NO: 7) are considered. Human U2OS cells both in untreated conditions and following arsenite-induced translational arrest and subsequent polysome disassembly. In wild-type (WT) cells, 400 µM arsenite treatment for 1-2 hours causes the formation of stress granules, as visualized by well-established stress granule markers. G3BP1/2 double-knockout U2OS cells were co-transduced to express mGFP-UBAP2L 467-540 (which is an FG-rich G3BP interaction domain) and G3BP1-mCherry. In cells featuring high UBAP2L 467-540 (FIG. 7A), stress granules did not form and G3BP1-mCherry remained diffuse throughout the cytoplasm. In cells expressing low UBAP2L 467-650 (FIG. 7B), stress granules (700) were apparent. Thus, the data suggests that similar to the USP10 FGDF motif ×1, this FG-rich UBAP2L peptide can bind to G3BP NTF2-like domain and inhibit higher-order interactions with other RNA-binding proteins. For these experiments, images were collected using 0.5 frames per second scan rate, 1024×1024 pixel frame, and 1.75× Nyquist zoom (63× oil immersion lens). Laser powers (1% 488 and 100% 546), intensities, and gains were kept constant.

Figure 7C:
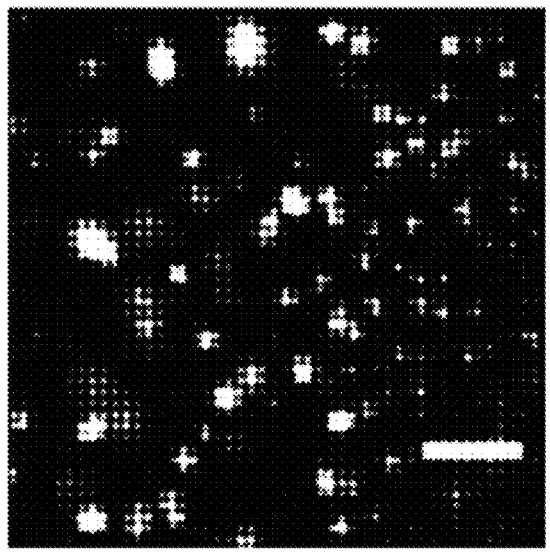
FIG. 7C is an image of a system including G3BP ΔRBD structures co-expressed with CAPRIN1-iRFP, illustrating the formation of clusters of the structures.
Figure 7D:
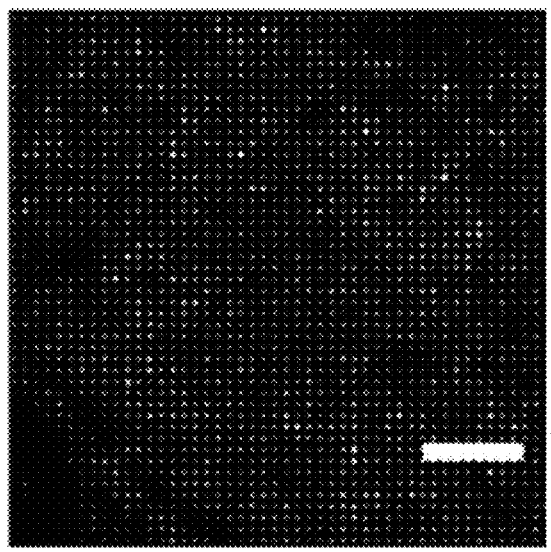
FIG. 7D is an image of a system including G3BP ΔRBD structures co-expressed with USP10-iRFP, illustrating the lack of clustered structures.

It is believed that NTF2-associated proteins collectively contribute the high RBD valency essential for stress granule condensation. Moreover, excess concentration of partners that lack RBDs (e.g., USP10, truncated G3BP, etc.) may inhibit this phase transition by out-competing binding of RBD-containing proteins (e.g., CAPRIN1 (SEQ ID NO: 8)). It is hypothesized that USP10 acts as a molecular shut-off valve for this system by causing a significant decrease in the RBD valency of the network, possibly by cutting protein-protein cross-links between G3BP nodes or "capping" the network. It is believed that such an off-switch would occur independently of additional weak RNA cross-links between oligomeric RBP nodes, and that strong multivalent NTF2-NTF2 interactions between engineered structures would be sufficient for phase separation of the associated protein network. In another experiment, structures comprising G3BP ΔRBD were co-expressed with CAPRIN1-iRFP (i.e., a G3BP NTF2-binding partner with RBD) or USP10-iRFP (i.e., NTF2-associated partner without RBD that competes for binding with CAPRIN1 and possibly other RBPs that confer additive valency to complex). As seen in FIG. 7C, excess CAPRIN1-iRFP binds with the structures, but does not prevent the clustering/phase separation of the structures comprising G3BP ΔRBD. However, as seen in FIG. 7D, excess USP10 completely blocks phase separation of the structures.

Figure 8A:
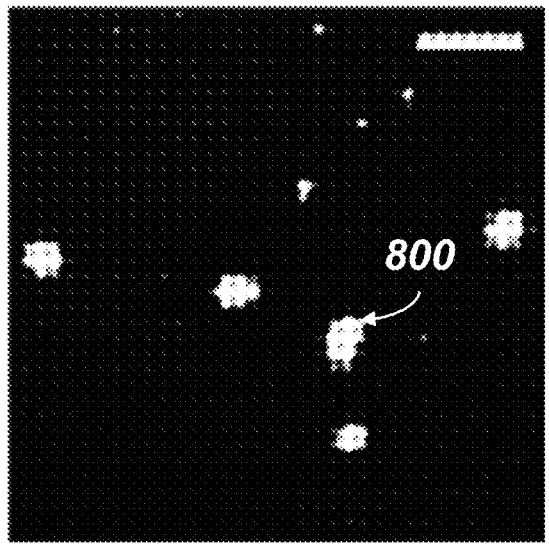
FIGS. 8A and 8B are images illustrating the existence of stress granules (800) in wild-type U2OS cells co-transduced with mGFP-USP10 FGDFx2 and YBX1-mCherry when activating the GFP (8A) and when activating the mCherry (8B) prior to arsenite treatment.
Figure 8B:
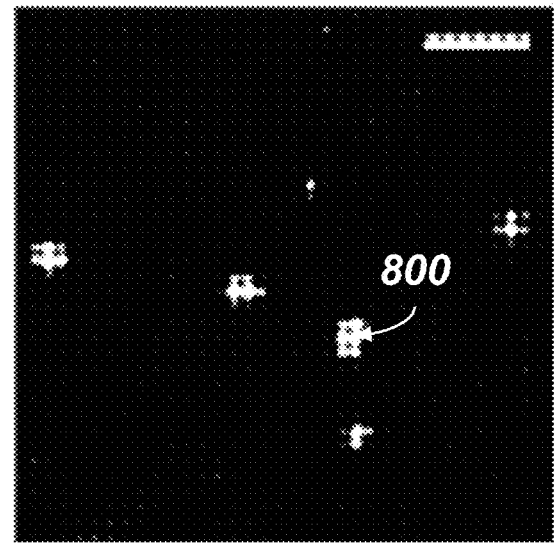

In an example illustrating the ability to increase stress granule assembly, the USP10 FGDF motif ×2 and YBX1 (SEQ ID NO: 9) are considered. YBX1 is an RNA-binding protein that marks stress granules and does not require G3BP1 NTF2-like domain for entry. Whereas the USP10 FGDF motif ×1 inhibits stress granule formation, the USP10 FGDF motif ×2 promotes stress granule biogenesis by cross-linking G3BP dimers into extended complexes that retain ability to interact with RNA. Wild-type U2OS cells were co-transduced with mGFP-USP10 FGDF motif ×2 and YBX1-mCherry. Even in the absence of stress (i.e. non-treated), stress granules (800) are observed for both the USP10 FGDF motif ×2 (FIG. 8A) and the YBX1 (FIG. 8B).

Figure 8C:
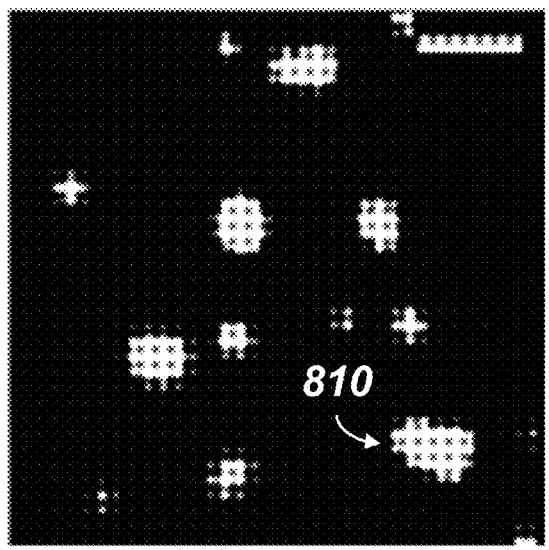
FIGS. 8C and 8D are images illustrating the existence of larger stress granules (810) in wild-type U2OS cells co-transduced with mGFP-USP10 FGDFx2 and YBX1-mCherry when activating the GFP (8A) and when activating the mCherry (8B) after arsenite treatment.
Figure 8D:
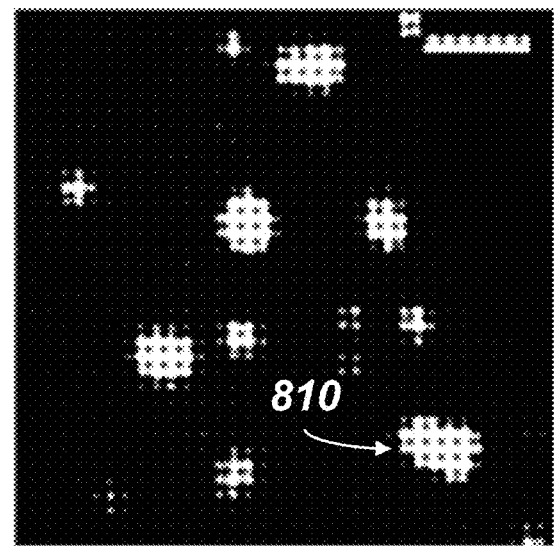

Larger granules (810) are observed following stress (arsenite) for both the USP10 FGDF motif ×2 (FIG. 8C) and the YBX1 (FIG. 8D).

Figure 5:
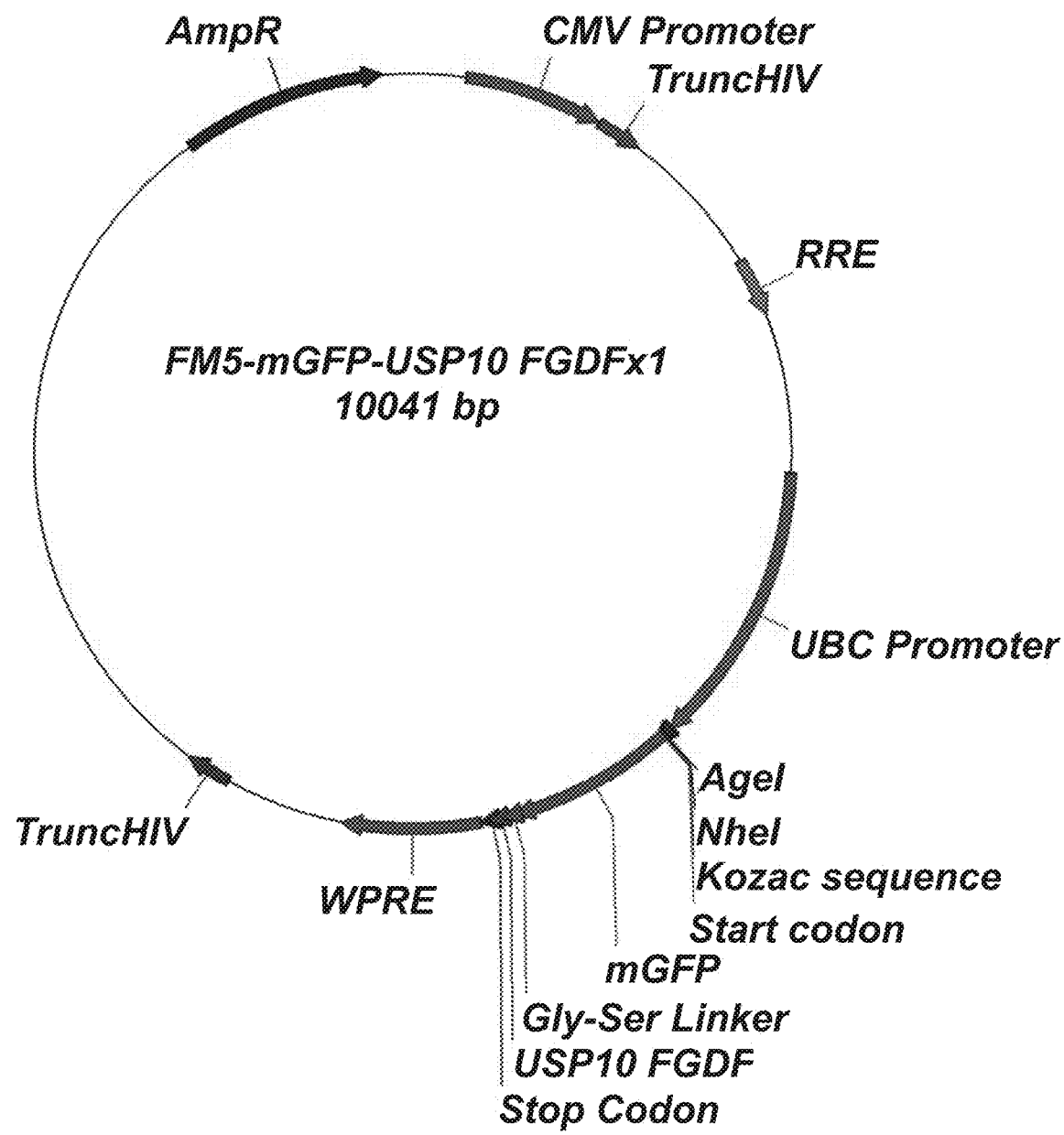
FIG. 5 is a gene map of an expression plasmid that expresses binding proteins but not a cell penetrating protein.

Also disclosed is a plasmid configured to express the protein construct described above. In one embodiment, the protein construct may be cloned into a custom lentiviral vector, allowing stable integration of the DNA into dividing human cells. The protein construct was expressed in mammalian cells using standard protocols of non-replication competent lentivirus infection and subsequent genomic integration. A gene map of a plasmid that expresses the binding proteins (but without the cell penetrating protein) can be seen in reference to FIG. 5. There, the plasmid incorporates a fluorophore sequence (mGFP) and a sequence for a USP10 FGDF motif ×1 described previously, under a UBC (Ubiquitin C) Promoter.

Also disclosed is a method of treating a disease or infection in a patient. In some cases, the patient has a neurodegenerative disease or disorder of cell proliferation (e.g., various cancers). In some cases, the method is a method for actively treating a disease or infection (e.g., actively treating a viral infection). In some cases, the method is used as a prophylactically treatment.

Figure 6:
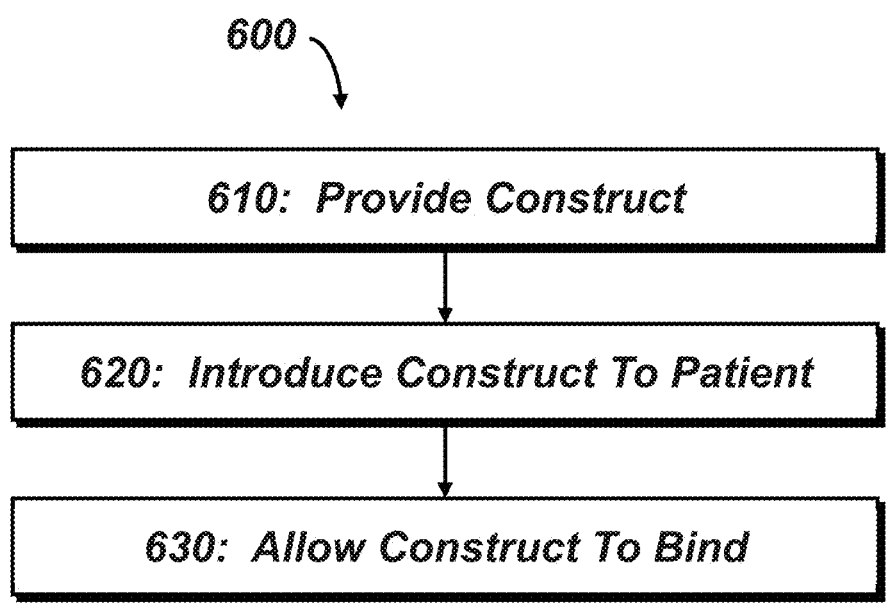
FIG. 6 is a flowchart of an embodiment of a method for treating a patient.

Referring to FIG. 6, the treatment method (600) broadly involves three steps.

The first step (610) is to provide a protein construct that is configured to penetrate a cell and bind with an NTF2-like domain. In some embodiments, the protein construct is provided by itself. In some embodiments, the protein construct is present in a fluid that is suitable for injection. The fluid may comprise water. In some embodiments, what may be provided is, e.g., a sterile package containing a fluid comprising less than 30% by weight of the protein construct.

The second step (620) is to introduce the protein construct (which includes any composition that comprises the protein construct) to a patient. This may be done by any appropriate technique known to those of skill in the art. In some embodiments the protein construct may be administered, e.g., orally, transdermally, or via intramuscular, subcutaneous, or intradermal injection. In some embodiments, the protein construct is injected into cerebrospinal fluid.

The third step (630) is to allow the protein construct to modulate pathological stress granule assembly. In some embodiments, where the protein construct consists of a single protein that binds with NTF2-like domains, the protein construct downregulates the formation of stress granules. In some embodiments, where the protein construct consists of two or more proteins that binds with NTF2-like domains, the protein construct upregulates the formation of stress granules.

In some embodiments, the protein construct hinders at least one homotypic or heterotypic interaction in the organism between an essential stress granule nucleator and itself or associating binding partners, preferably without causing immediate cell toxicity.

Those skilled in the art will recognize or be able to ascertain using no more than routine experimentation, many equivalents to the specific embodiments of the invention described herein. Such equivalents are intended to be encompassed by the following claims.

What is claimed is:

1. A protein construct for use in upregulating stress granule formation comprising:
   a cell penetrating protein fused to k binding proteins that can bind to a NTF2-like domain, each binding protein comprises the first 142 amino acids of G3BP1, wherein 1<k≤10.

2. The protein construct according to claim 1, wherein the cell penetrating protein is further fused to a protein tag.

3. The protein construct according to claim 2, wherein the protein tag is a fluorescent protein.

4. A plasmid configured to express the protein construct according to claim 1.

5. A method of treating a disease or infection in a patient, comprising the steps of:
   providing the protein construct of claim 1; and
   introducing the protein construct to the patient so as to allow the protein construct to bind with at least one NTF2-like domain within the cell, wherein formation of stress granules is modulated.

6. The method according to claim 5, wherein the protein construct is introduced as a prophylactic treatment.

7. The method according to claim 6, wherein the protein construct is introduced as an active treatment of a viral infection.

8. A method of treating a disease or infection in a patient, comprising the steps of:
   providing fluid comprising the protein construct of claim 1; and injecting the fluid into a patient at a location that allows the protein construct to upregulate pathological stress granule assembly.

9. The method according to claim 8, wherein the patient has a neurodegenerative disease or disorder of cell proliferation.

10. The method according to claim 8, wherein the protein construct is injected into cerebrospinal fluid.

11. The method according to claim 8, wherein the protein construct hinders at least one homotypic or heterotypic interaction in the organism between an essential stress granule nucleator and itself or an associating binding partner without causing immediate cell toxicity.

12. The method of claim 5, wherein the patient has a neurodegenerative disease.

13. The method of claim 5, wherein the patient has a cell proliferative disorder.

\* \* \* \* \*